United States Patent [19]
Allam et al.

[11] Patent Number: 6,117,916
[45] Date of Patent: Sep. 12, 2000

[54] INTEGRATION OF A CRYOGENIC AIR SEPARATOR WITH SYNTHESIS GAS PRODUCTION AND CONVERSION

[75] Inventors: Rodney John Allam, Guildford; Angela Sheldon, Walton-on-Thames, both of United Kingdom

[73] Assignee: Air Products and Chemicals, Inc., Allentown, Pa.

[21] Appl. No.: 09/232,954

[22] Filed: Jan. 18, 1999

[30] Foreign Application Priority Data

Jan. 20, 1998 [GB] United Kingdom .................. 9801200

[51] Int. Cl.[7] .......................... C07C 27/00; C07C 27/06; C07C 1/02; C01B 3/24; F28D 7/00
[52] U.S. Cl. ........................ 518/702; 518/703; 252/373; 423/650; 423/651; 422/194; 422/196; 422/200
[58] Field of Search ........................... 252/373; 423/650, 423/651; 518/702, 703; 422/200, 194, 196

[56] References Cited

U.S. PATENT DOCUMENTS 4,461,154  7/1984  Allam ............................................ 62/87
5,635,541  6/1997  Smith et al. .............................. 518/703

*Primary Examiner*—Steven P. Griffin
*Assistant Examiner*—Jonas N. Strickland
*Attorney, Agent, or Firm*—Willard Jones, III

[57] ABSTRACT

The invention provides an improvement in the utilization of hydrocarbon feedstock by partial oxidation with oxygen to form a synthesis gas comprising carbon monoxide and hydrogen and subjecting the synthesis gas to a conversion process comprising an exothermic reaction. The oxygen is provided by air separation in which the feed air is at least partially compressed by work generated by expansion of a working fluid vaporized by indirect heat exchange with at least one of the synthesis gas and the exothermic reaction. The improvement is that the working fluid is preheated by indirect heat exchange with adiabatically compressed feed air, thereby improving the overall efficiency of the process and reducing capital costs compared with conventional generally isothermal feed air compression. Preferably, the gas conversion process is a catalytic hydrogenation to prepare paraffinic hydrocarbons (Fischer-Tropsch reaction), methanol or dimethylether.

23 Claims, 3 Drawing Sheets

6,117,916

INTEGRATION OF A CRYOGENIC AIR SEPARATOR WITH SYNTHESIS GAS PRODUCTION AND CONVERSION

TECHNICAL FIELD OF THE INVENTION

The present invention relates to the integration of elevated pressure air separation with the production of a synthesis gas containing hydrogen and carbon monoxide (CO) from a hydrocarbon feedstock using oxygen obtained by air separation and subsequent use of the synthesis gas by an exothermic conversion process. It has particular, but not exclusive, application to the partial oxidation of natural gas and the conversion of the resultant synthesis gas to a liquid product by a catalytic hydrogenation process. The term "partial oxidation" used in this Application in respect of natural gas or other hydrocarbon feedstock means any reaction of the feedstock to produce synthesis gas which involves the use of oxygen even if conducted in the presence of steam or other reactive component unless it is clear from the context that only reaction with oxygen is intended.

BACKGROUND OF THE INVENTION

Natural gas is often produced, either in association with crude oil or on its own, in a remote location where it is not economic to transport the gas to use points with pipelines. One method of recovering this gas is to convert it to paraffinic hydrocarbons or their oxygenated derivatives by catalytic hydrogenation. The term "catalytic hydrogenation" is used in this Application to mean contacting the gas with a catalyst whereby carbon monoxide in the gas is hydrogenated by the hydrogen content of the gas to produce paraffinic hydrocarbons or oxygenated derivatives, especially methanol and dimethylether but also aldehydes and ketones. The term "Fischer-Tropsch process" means such catalytic hydrogenation to prepare paraffinic hydrocarbons. Other uses of synthesis gas include the preparation of ammonia. These gas conversion processes are exothermic and conventionally the heat of reaction is used to generate steam.

The conversion of natural gas (or other hydrocarbon feedstock) to synthesis gas is accomplished using one of several standard methods available such as steam reforming, autothermal reforming, combined steam and autothermal reforming, combined reforming with pre-reforming partial oxidation and gas heated reforming etc. The most favourable systems to minimise overall equipment size and cost of production use processes in which oxygen is separated from air and used in, for example, an autothermal, combined reformer or partial oxidation system. The use of oxygen allows the production of synthesis gas having the high $CO:H_2$ ratio (about 1:1.6 to about 1:2.5) required for a catalytic hydrogenation process without excess hydrogen production.

U.K. Patent publication No. 2237287 A discloses a methanol synthesis in which the feedstock is provided by reformed natural gas. The reforming is conducted with oxygen-enriched air and part of the reformed gas is subjected to a carbon monoxide shift reaction and the hydrogen content of the resultant gas stream mixed with the remainder of the reformed gas to provide a hydrogen-enriched feedstock for the methanol synthesis.

European Patent publication No. 0634562 A discloses an integrated air separation-gas turbine power generation process in which synthesis gas is combusted with saturated, compressed gas turbine feed air to provide a combustion gas which is work expanded in the gas turbine to drive gas turbine feed air compressor(s) and provide power. The synthesis gas is prepared by reaction of a carbonaceous fuel with compressed air separation unit ("ASU") oxygen product. At least part of the ASU feed air is provided from a gas turbine compressor. The water used to saturate the compressed gas turbine feed air prior to combustion is heated using the heat of compression of the ASU oxygen product prior to synthesis gas production.

U.S. Pat. No. 4,888,131 (Goetsch et al) and U.S. Pat. No. 5,160,456 (Lahn et al) both describe the partial oxidation of natural gas with oxygen to produce synthesis gas and the conversion of that gas into liquid products by a Fischer-Tropsch process ("remote gas process") but do not describe the ASU used. Further information on the remote gas process is provided in a paper by Ansell et al ("Liquid/fuels from Natural Gas—An Update of the Exxon Process") presented at the Council on Alternate Fuels, Apr. 26–28, 1994 but again there are no details of the ASU.

A paper by Tijm et al ("Shell Middle Distillate Synthesis The Process, The Products, The Plant") presented at the Council on Alternate Fuels, Apr. 26–29, 1994 gives a summary of the remote gas process developed by Shell, but does not provide any details of the ASU.

A paper by Choi et al ("Design/Economics of a natural gas based Fischer-Tropsch plant") presented at the AIChemE 1997 Spring National Meeting Mar. 9–13, 1997 gives further economic and design information of a remote gas process but no information on the ASU.

International Patent Application No. WO 97/12118 (PCT/NO96/00227) has a detailed process description of, and provides heat and material balances for, a remote gas process but again fails to provide ASU details.

U.S. Pat. No. 5,635,541 (Smith et al) describes a remote gas process in which part of the steam generated by the gas conversion reaction is used to drive the gas compression requirements of an elevated pressure ASU.

Conventionally, the air feed for an ASU is compressed in a generally isothermal manner using a multistage compressor with intercoolers. Little, if any, useful energy can be recovered from the intercoolers. However, U.S. Pat. No. 4,461,154 (Allam) teaches that, at a sufficiently high compression ratio (at least 2.5:1), generally adiabatic compression of a gas produces a temperature sufficiently high to provide high grade energy which can be used directly or indirectly to assist in driving the compressor. The energy produced compensates for the additional power required for the adiabatic compression.

In particular, U.S. Pat. No. 4,461,154 describes an air compression system having a steam turbine drive in which the air is compressed adiabatically; the compressed air leaving the compressor is passed through an aftercooler where it heats boiler feedwater; the heated boiler feedwater is vaporized in the boiler producing superheated steam; and the steam used to drive the air compressor. The preheating of the boiler feedwater allows the excess heat in the boiler flue gas to be used for preheating air fed to the boiler for fuel combustion. The arrangement allows a substantial reduction in the fuel consumption for steam production. Further, the weight, volume, cost, footprint, and height of an adiabatic compressor are all considerably smaller than for a multistage compressor with intercoolers as used in conventional ASUs.

It is an object of this invention to integrate an ASU with synthesis gas production and conversion in a cost effective manner suitable for remote gas processing. It is a further object of the invention to integrate air separation and natural gas utilization for ease of installation on an offshore gas or gas/oil production platform or floating production storage and offloading system (FPSO). Other objects are to minimise the volume and weight of the ASU; to minimise the cost of the total facility power system by optimising the backup power supply required for start-up and operation of the ASU; and to more efficiently utilise the excess energy (usually in the form of steam) available from the gas conversion. Some or all of these objectives are achieved in varying degrees by processes of the present invention. Although the invention has been developed to meet these objectives, it is not limited to application in remote locations or to the use of natural gas but is of general application where appropriate conditions and requirements exist.

SUMMARY OF THE INVENTION

In a first aspect, the present invention is an improvement in a process for the utilization of a hydrocarbon feedstock in which the feedstock is partially oxidized using oxygen provided by air separation to form a synthesis gas comprising carbon monoxide and hydrogen and the synthesis gas is subjected to a conversion process comprising an exothermic reaction, and wherein the feed air for the air separation is at least partially compressed by work generated by expansion of a working fluid vaporized by indirect heat exchange with at least one of the synthesis gas and the exothermic reaction. The improvement consists in compressing the feed air in an adiabatic manner to provide preheat to the working fluid by indirect heat exchange with the compressed air.

Optionally other plant gas compressors can be generally adiabatic compressors to supplement the preheat provided by the feed air compressor.

In another aspect, the invention is a corresponding improvement in the apparatus used for the feedstock utilization. This improvement is the provision of an adiabatic feed air compressor to provide heated air for preheating the working fluid, a heat exchanger for indirect heat exchange between the adiabatically compressed feed air and the working fluid to preheat the working fluid, and conduit means for conveying said preheated working fluid to vaporization means vaporizing the working fluid by heat exchange against the synthesis gas or exothermic reaction.

DETAILED DESCRIPTION OF THE INVENTION

Figure 1:
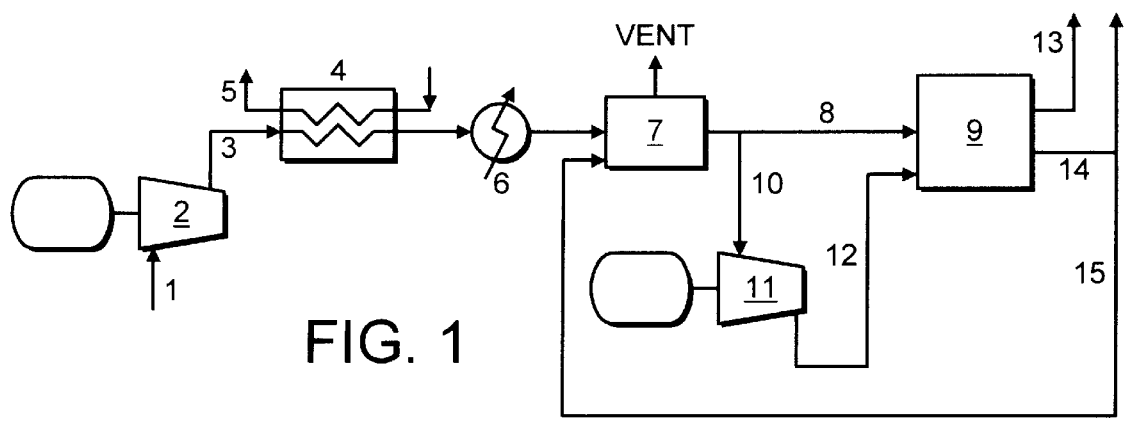
FIG. 1 is a schematic representation of an air separation process for incorporation in a process in accordance with the present invention.

According to the present invention, there is provided an improvement in a process for the utilization of a hydrocarbon feedstock by partially oxidizing the feedstock with oxygen to form a synthesis gas comprising carbon monoxide and hydrogen and subjecting the synthesis gas to a conversion process comprising an exothermic reaction, said oxygen being provided by air separation in which the feed air is at least partially compressed by work generated by expansion of a working fluid vaporized by indirect heat exchange with at least one of the synthesis gas and the exothermic reaction, the improvement consisting in that the working fluid is preheated by indirect heat exchange with adiabatically compressed feed air.

The present invention also provides an improvement in an apparatus for the utilization of a hydrocarbon feedstock comprising a feedstock reactor for partially oxidizing the feedstock with oxygen to form a synthesis gas comprising carbon monoxide and hydrogen; a synthesis gas conversion reactor for subjecting the synthesis gas to a conversion process comprising an exothermic reaction; an air separation unit for separation of air to supply oxygen to the feedstock reactor and including a feed air compressor; a working fluid circuit including vaporization means for vaporizing the working fluid by indirect heat exchange with at least one of the synthesis gas and the exothermic reaction and an expander for producing work by expansion of the vaporized working fluid; and means coupling said expander to the feed air compressor whereby the feed air is at least partially compressed by work generated by the expander, the improvement consisting in that the feed air compressor is an adiabatic compressor providing heated air for preheating the working fluid and the working fluid circuit includes a heat exchanger for indirect heat exchange between the adiabatically compressed feed air and the working fluid to preheat the working fluid and conduit means for conveying said preheated working fluid to said vaporization means.

When the synthesis gas conversion process is a Fischer-Tropsch reaction, a large amount of heat is generated. The reaction can be represented as:

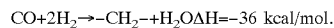

$$CO+2H_2 \rightarrow -CH_2-+H_2O \quad \Delta H=-36 \text{ kcal/mol}.$$

Less but still significant heat is generated when the process is a catalytic hydrogenation producing methanol and this reaction can be represented as:

$$CO+2H_2 \rightarrow CH_3OH \quad \Delta H=-24 \text{ kcal/mol}.$$

Other exothermic synthesis gas conversion processes include the production of dimethylether from methanol formed in situ from the synthesis gas and the production of ammonia in which the exothermic reaction is the reaction of the hydrogen content of synthesis gas with nitrogen, which can be provided by the air separation process.

The synthesis gas conversion reactors usually are operated under generally isothermal conditions with the heat of reaction being removed by generating steam from heat exchange tubes within the reactor. The synthesis gas feed is produced in a high temperature reactor system utilising oxygen such as a partial oxidation reactor or an autothermal reforming reactor. The high temperature synthesis gas leaving the reactor needs to be cooled to the operating temperature of the gas conversion reactor, which is typically 220 to 280° C. when preparing paraffinic hydrocarbons. The heat removed by said cooling could be used to generate high pressure steam for shaft power production. However, the gas conversion exothermic reaction is characterised by the liberation of all the heat at or above the temperature of the reaction and there is not enough heat available below this temperature level in the conventional process to provide all the low level heat required for feedwater preheating to supply the steam system. Use of an adiabatic feed air compressor in accordance with the present invention provides heat at a high enough temperature level to supply at least part of the feedwater preheating duty.

There are several advantages in using an adiabatic feed air compressor. Since it has no intercoolers, it is compact, relatively low in weight, has a small height and a small footprint compared to an intercooled compressor. There is no need for large cooling water flows to the compressor; usually a single trim cooler will be provided following the feed air/working fluid heat exchanger. These features make it easy to modularise the compression system and they are particularly desirable for offshore gas processing systems such as fixed platforms or an FPSO. The adiabatic compressors usually would be driven either by steam turbines or by electric motors with electricity generated from a steam turbine system with additional gas turbine backup.

Usually, the air separation will be cryogenic air separation but other elevated pressure air separation processes, especially pressure swing adsorption, can be used.

The feedstock usually will be natural gas but any other hydrocarbon feedstock conventionally used as a source of synthesis gas can be used.

The partial oxidation can be conducted by any of the known processes for producing synthesis gas which use oxygen but preferably is a process producing a gas having a carbon monoxide: hydrogen mole ratio of from about 1:1.6 to about 1:2.5.

Usually, the working fluid will be water.

The working fluid can be vaporized by indirect heat exchange with the synthesis gas and/or with the exothermic reaction. Usually, a first vaporized working fluid stream at a first pressure, for example about 10 to about 30 bara (1 to 3 MPa), provided by indirect heat exchange with the exothermic reaction and a second vaporized working fluid stream at a higher pressure, for example about 60 bara (6 MPa) is provided by indirect heat exchange with the synthesis gas and both vaporized working fluid streams are expanded to contribute to air compression requirement work.

The liquid working fluid preheated by indirect heat exchange with the adiabatically compressed air is supplied to the exothermic reaction heat exchange and/or to the synthesis gas heat exchange but usually will be supplied to the exothermic reaction heat exchange.

The following is a description, by way of example only and with reference to the accompanying drawings, of presently preferred embodiments of the present invention.

Referring first to FIG. 1, a cryogenic air separation system comprises an axial flow adiabatic compressor 2 which compresses feed air 1 from ambient pressure to 5.5 bara. (0.55 MPa) and thereby raises its temperature from 20° C. to 240° C. The compressed air 3 is cooled in an aftercooler 4 against 28 bar (2.8 MPa) feedwater to provide a preheated feedwater stream 5 at 230° C. The thus cooled feed air is further cooled to 20° C. in a trim cooler 6 before entering an air purification absorber 7. Dry purified air leaving the absorber is split into a first substream 8, which is fed directly to a cryogenic air separator 9, and a second substream 10, which is further compressed to 60 bar (6 MPa) in an intercooled multistage centrifugal compressor 11 before also being fed 12 to the separator 9. The feed air substreams 8,12 are separated in separator 9 by cryogenic distillation using a conventional pumped oxygen cycle to provide oxygen 13 at 40 bar (4 MPa) and waste nitrogen 14, a substream 15 of which is used for regeneration of absorber 7. Optionally the booster compressor 11 could be an adiabatic compressor with an aftercooler heating feedwater followed by a trim cooler.

Figure 2:
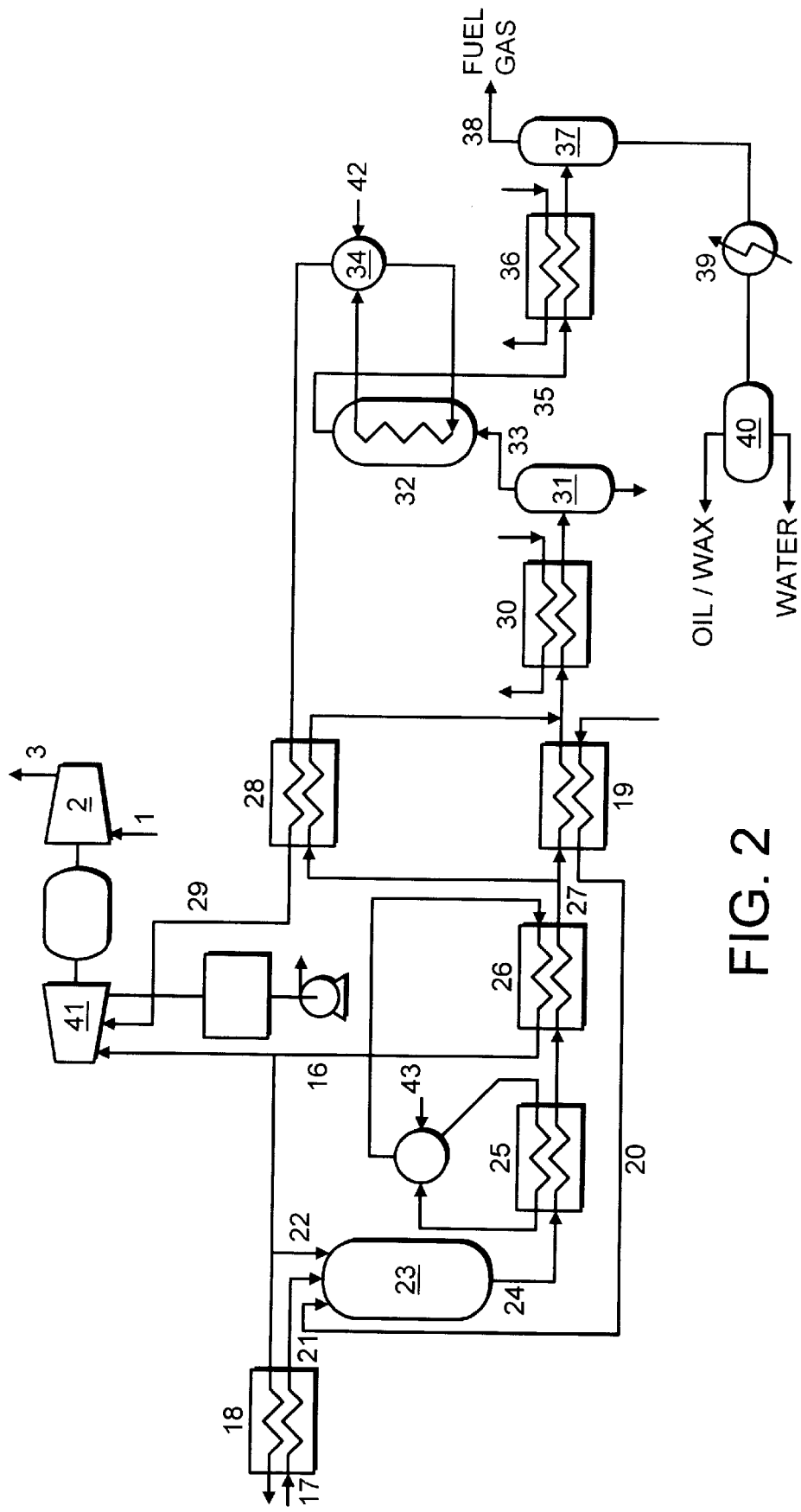
FIG. 2 is a schematic representation of an integrated synthesis gas production and Fischer-Tropsch process for incorporation with the air separation process of FIG. 1.

The compressor 2 is driven via an electric generator/motor by a steam turbine 41 powered by steam generated in a gas conversion process (see FIG. 2). Oxygen 17 at 40 bar (4 MPa) and 20° C. supplied from the air separator 9 enters via line 17 and is preheated to 270° C. against condensing 60 bar (6 MPa) steam in heat exchanger 18. Natural gas at 40 bar (4 MPa) is preheated to 270° C. in heat exchanger 19 and fed 20, with the hot oxygen 21 and steam 22, into the burner of a partial oxidation reactor 23. The proportion of steam, oxygen and natural gas are such that the synthesis gas 24 produced has a hydrogen:carbon monoxide ratio of 2.14:1.

The synthesis gas 24 leaves the reactor 23 at 1083° C. and is cooled in a waste heat boiler 25 to generate 60 bar (6 MPa) steam which is then superheated to 430° C. in a synthesis gas cooler 26 to provide high pressure steam 16 for the turbine 41, reactor 23 and heat exchanger 18. The synthesis gas 27 leaving the cooler 26 is at 290° C. and is divided into two substreams which are cooled in heat exchanger 19 and parallel heat exchanger 28, which superheats steam from a synthesis gas conversion slurry reactor 32 to provide 28 bar (2.8 MPa) steam 29 at 270° C. The synthesis gas is then further cooled to 40° C. in heat exchanger 30 in which 60 bar (6 MPa) feedwater is preheated. Water is separated from the synthesis gas in the separator 31 and the residual synthesis gas 33 enters the slurry reactor 32 for Fischer-Tropsch conversion into paraffinic hydrocarbons. The heat generated in the reactor 32 is removed by evaporating water at 28 bar (2.8 MPa) which maintains the reactor temperature at 250° C. Saturated steam is produced from a steam drum 34 to supply the heat exchanger 28. Clean reactor effluent 35 is cooled to 150° C. in a heat exchanger 36 to preheat feedwater at 28 bar (2.8 MPa) and the residual gas is separated from paraffinic hydrocarbon liquid product in a separator 37. The gas 38 provides fuel to a gas turbine power generation system (not shown) and the separated liquid product is cooled close to ambient temperature against cooling water in a heat exchanger 39. The cooled liquid is fed to a decanter vessel 40 where paraffinic hydrocarbons are separated from water.

60 Bar (6 MPa) steam from cooler 26 and 28 bar (2.8 MPa) steam 29 are expanded in steam turbine 41, which is coupled to an electric generator/motor which also drives the main ASU air compressor 2. The system can be started by driving the electric motor and main air compressor using electric power supplied by a gas turbine using the fuel gas 38.

The 28 bar (2.8 MPa) feedwater requirement 42 of the system is provided by preheated feedwater 5 from the aftercooler 4 and preheated feedwater from heat exchanger 36 and the 60 bar (6 MPa) feedwater requirement 43 is provided by the preheated feedwater from the heat exchanger 30. If required, the preheated feedwater 5 could be at 60 bar (6 MPa) and used to supplement the preheated 60 bar feedwater from heat exchanger 30 instead of the preheated 28 bar (2.8) feedwater from heat exchanger 36. In a further alternative, heat exchanger 4 could heat two feedwater streams, one at 60 bar (6 MPa) and the other at 28 bar (2.8 MPa), to supplement preheated feedwater from both of the heat exchangers 30,36.

The exhaust steam is recycled to the system in conventional manner after condensation and deaeration.

Table I gives a summary of the main operating conditions for the process of FIGS. 1 and 2 without feedwater preheating by the adiabatic air compressor 2.

TABLE I

| | Stream No. | | | | | | | | | | |
|---|---|---|---|---|---|---|---|---|---|---|---|
| | 20 | 21 | 22 | 24 | 27 | 33 | 35 | 38 | Oil/Wax | 16 | 29 |
| Mole Fraction | | | | | | | | | | | |
| $O_2$ | 0 | 0.9950 | 0 | 0 | 0 | 0 | 0 | 0 | 0 | 0 | 0 |
| $N_2$ | 0.0052 | 0.0050 | 0 | 0.0021 | 0.0021 | 0.0028 | 0.0054 | 0.0082 | 2.373E-04 | 0 | 0 |
| $CH_4$ | 0.8608 | 0 | 0 | 0.0079 | 0.0079 | 0.0102 | 0.0442 | 0.0675 | 0.0018 | 0 | 0 |
| CO | 0 | 0 | 0 | 0.2268 | 0.2268 | 0.2926 | 0.0661 | 0.1316 | 0.0025 | 0 | 0 |
| $H_2$ | 0 | 0 | 0 | 0.4854 | 0.4854 | 0.6261 | 0.2129 | 0.3254 | 0.0059 | 0 | 0 |
| $CO_2$ | 0.0161 | 0 | 0 | 0.0509 | 0.0509 | 0.0655 | 0.1351 | 0.2057 | 0.0162 | 0 | 0 |
| $H_2O$ | 0 | 0 | 1 | 0.2269 | 0.2269 | 0.0030 | 0.4808 | 0.2469 | 0.0130 | 1 | 1 |
| $C_2H_6$ | 0.0802 | 0 | 0 | 0 | 0 | 0 | 0.0022 | 0.0034 | 1.489E-04 | 0 | 0 |
| $C_3H_8$ | 0.0266 | 0 | 0 | 0 | 0 | 0 | 0.0022 | 0.0034 | 1.451E-04 | 0 | 0 |
| $C_4H_{10}$ | 0.0057 | 0 | 0 | 0 | 0 | 0 | 0.0022 | 0.0034 | 1.716E-04 | 0 | 0 |
| $i-C_4H_{10}$ | 0.0029 | 0 | 0 | 0 | 0 | 0 | 0 | 0 | 0 | 0 | 0 |
| $C_5H_{12}$ | 9.0E-04 | 0 | 0 | 0 | 0 | 0 | 0.0022 | 0.0033 | 1.404E-04 | 0 | 0 |
| $IC_5H_{12}$ | 0.0010 | 0 | 0 | 0 | 0 | 0 | 0 | 0 | 0 | 0 | 0 |
| $C_6H_{14}$ | 5.0E-04 | 0 | 0 | 0 | 0 | 0 | 0 | 0 | 0 | 0 | 0 |
| $C_7H_{16}$ | 1.0E-04 | 0 | 0 | 0 | 0 | 0 | 0 | 0 | 0 | 0 | 0 |
| $C_{16}H_{34}$ (Average) | 0 | 0 | 0 | 0 | 0 | 0 | 0.0267 | 0.0011 | 0.9597 | 0 | 0 |
| Total Flow kmol/h | 1863.51 | 1302.98 | 1568.68 | 7599.48 | 7599.48 | 5890.62 | 3000.64 | 1961.85 | 81.13 | 5980.00 | 6194.00 |
| Temperature ° C. | 270.00 | 270.00 | 250.21 | 1083.86 | 290.00 | 40.00 | 250.00 | 150.00 | 92.96 | 430.00 | 270.00 |
| Pressure bara | 40 | 40 | 40 | 40 | 28 | 28 | 28 | 28 | 28 | 60 | 28 |
| Pressure MPa | 4.0 | 4.0 | 4.0 | 4.0 | 2.8 | 2.8 | 2.8 | 2.8 | 2.8 | 6.0 | 2.8 |

Table II shows the quantity of 60 bar (6 MPa) and 28 bar (2.8 MPa) steam produced and the required feedwater preheat duty compared with the total available from heat exchangers 30 and 36. The deficiency is 21.69 MW. The duty available from the ASU main air compressor aftercooler 4 is 10.2 MW. Optionally, the use of an adiabatic booster compressor 11 can provide a further 4.8 MW.

TABLE II

| | | |
|---|---|---|
| Steam Produced | 60 bar (6 MPa) steam | 29.9 kg/s |
| | 28 bar (2.8 MPa) steam | 30.97 kg/s |
| Preheat Required | 60 bar (6 MPa) steam | 35.39 MW |
| | 28 bar (2.8 MPa) steam | 27.87 MW |
| | Total required | 63.26 MW |
| Preheat Available | Heat exchanger 30 | 27.61 MW |
| | Heat exchanger 36 | 13.96 MW |
| | Total available | 41.57 MW |
| Preheat Deficiency | | 21.69 MW |

Figure 3:
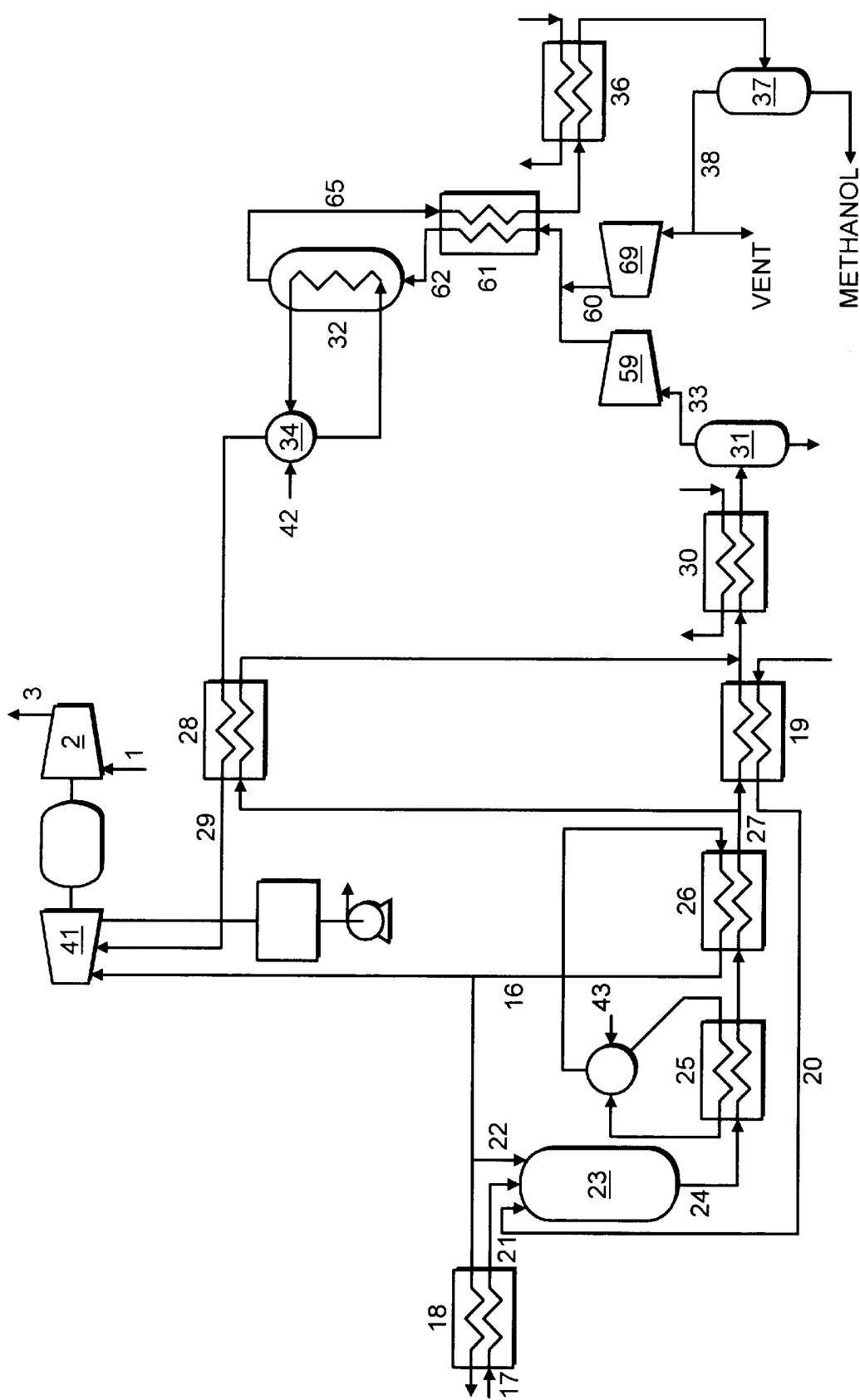
FIG. 3 is a schematic representation of an integrated synthesis gas production and methanol production for incorporation with the air separation process of FIG. 1.

FIG. 3 shows a gas conversion process similar to that of FIG. 2 but in which the synthesis gas is converted into methanol. The same reference numerals are used for corresponding items and only the main differences between the two processes are described.

The synthesis gas leaving the partial oxidation reactor 23 in line 24 is at 1091° C. and, after cooling in the heat exchangers 25, 26, 19, 28 & 30 and passage through the separator 31, is compressed to 70 bar (7 MPa) in a compressor 59 and mixed with a recycle stream 60. The combined stream is preheated to 240° C. in a heat exchanger 61 before it enters the methanol reactor system 32 via line 62. The heat generated in the methanol reactor 32 is removed by evaporating water at 28 bar (2.8 MPa) which maintains the reactor temperature at 250° C. Saturated steam is produced from the steam drum 34. The clean reactor effluent in line 65 is used in the heat exchanger 61 to preheat the synthesis gas entering the methanol reactor. The effluent stream is then cooled to 38° C. in heat exchanger 36 and the methanol stream separated from the residual gas in line 38 in separator 37. A portion of this residual gas is recompressed to 70 bar (7 MPa) in a compressor 69 and recycled to the process via line 60.

Table III gives a summary of the main operating conditions for the process of FIG. 3.

TABLE III

| | Stream No. | | | | | | | | | | | | |
|---|---|---|---|---|---|---|---|---|---|---|---|---|---|
| | 20 | 21 | 22 | 24 | 16 | 27 | 29 | 33 | 60 | 62 | 65 | Methanol | 38 |
| Mole Fraction | | | | | | | | | | | | | |
| $C_2$ | 0 | 0.9950 | 0 | 0 | 0 | 0 | 0 | 0 | 0 | 0 | 0 | 0 | 0 |
| $N_2$ | 0.0052 | 0.0050 | 0 | 0.0022 | 0 | 0.0022 | 0 | 0.0028 | 0.0122 | 0.0075 | 0.0100 | 2.912E-04 | 0.0122 |
| $CH_4$ | 0.8608 | 0 | 0 | 0.0076 | 0 | 0.0076 | 0 | 0.0098 | 0.0418 | 0.0259 | 0.0345 | 0.0020 | 0.0418 |
| CO | 0 | 0 | 0 | 0.2320 | 0 | 0.2320 | 0 | 0.2967 | 0.2423 | 0.2693 | 0.1987 | 0.0056 | 0.2423 |
| $H_2$ | 0 | 0 | 0 | 0.4896 | 0 | 0.4896 | 0 | 0.6261 | 0.5265 | 0.5758 | 0.4306 | 0.0056 | 0.5265 |
| $CO_2$ | 0.0161 | 0 | 0 | 0.0491 | 0 | 0.0491 | 0 | 0.0626 | 0.1696 | 0.1166 | 0.1495 | 0.0605 | 0.1696 |
| $H_2O$ | 0 | 0 | 1 | 0.2194 | 1 | 0.2194 | 1 | 0.0022 | 9.906E-05 | 0.0011 | 0.0070 | 0.0375 | 9.906E-05 |
| $C_2H_6$ | 0.0802 | 0 | 0 | 0 | 0 | 0 | 0 | 0 | 0 | 0 | 0 | 0 | 0 |
| $C_3H_8$ | 0.0266 | 0 | 0 | 0 | 0 | 0 | 0 | 0 | 0 | 0 | 0 | 0 | 0 |
| $C_4H_{10}$ | 0.0057 | 0 | 0 | 0 | 0 | 0 | 0 | 0 | 0 | 0 | 0 | 0 | 0 |
| $i-C_4H_{10}$ | 0.0029 | 0 | 0 | 0 | 0 | 0 | 0 | 0 | 0 | 0 | 0 | 0 | 0 |
| $C_5H_{12}$ | 9.0E-04 | 0 | 0 | 0 | 0 | 0 | 0 | 0 | 0 | 0 | 0 | 0 | 0 |

TABLE III-continued

| | Stream No. | | | | | | | | | | | | |
|---|---|---|---|---|---|---|---|---|---|---|---|---|---|
| | 20 | 21 | 22 | 24 | 16 | 27 | 29 | 33 | 60 | 62 | 65 | Methanol | 38 |
| $iC_5H_{12}$ | 0.0010 | 0 | 0 | 0 | 0 | 0 | 0 | 0 | 0 | 0 | 0 | 0 | 0 |
| $C_6H_{14}$ | 5.0E-04 | 0 | 0 | 0 | 0 | 0 | 0 | 0 | 0 | 0 | 0 | 0 | 0 |
| $C_7H_{16}$ | 1.0E-04 | 0 | 0 | 0 | 0 | 0 | 0 | 0 | 0 | 0 | 0 | 0 | 0 |
| $CH_3OH$ | 0 | 0 | 0 | 0 | 0 | 0 | 0 | 0 | 0.0075 | 0.0038 | 0.1697 | 0.8885 | 0.0075 |
| Total Flow kmol/h | 1864.10 | 1302.98 | 1479.58 | 7517.60 | 5966.00 | 7517.60 | 4394.00 | 5878.48 | 5990.45 | 11868.77 | 8927.70 | 1644.16 | 7283.54 |
| Temperature ° C. | 270.00 | 270.00 | 250.21 | 1091.45 | 430.00 | 290.00 | 270.00 | 40.00 | 43.84 | 240.00 | 250 | 37.83 | 37.83 |
| Pressure bara | 40 | 40 | 40 | 40 | 60 | 40 | 28 | 40 | 70 | 70 | 70 | 66 | 66 |
| Pressure MPa | 4.0 | 4.0 | 4.0 | 4.0 | 6.0 | 4.0 | 2.8 | 4.0 | 7.0 | 7.0 | 7.0 | 6.6 | 6.6 |

Table IV shows the quantity of 60 bar (6 MPa) and 28 bar (2.8 MPa) steam produced in the process of FIG. 3 and the required feedwater preheat duty compared with the total available from heat exchangers 30 and 36. The deficiency is 10.71 MW. The duty available from the ASU main air compressor aftercooler 4 is 10.2 MW. Optionally, the use of an adiabatic booster compressor 11 can provide a further 4.8 MW.

TABLE IV

| | | |
|---|---|---|
| Steam Produced | 60 bar (6 MPa) steam | 29.83 kg/s |
| | 28 bar (2.8 MPa) steam | 21.97 kg/s |
| Preheat Required | 60 bar (6 MPa) steam | 35.32 MW |
| | 28 bar (2.8 MPa) steam | 19.77 MW |
| | Total required | 55.09 MW |
| Preheat Available | Heat exchanger 30 | 27.48 MW |
| | Heat exchanger 36 | 16.90 MW |
| | Total available | 44.38 MW |
| Preheat Deficiency | | 10.71 MW |

The use of adiabatic compression thus improves the overall efficiency of the processes of FIGS. 2 and 3, while at the same time, achieving the advantages of compactness, low weight, etc. mentioned previously, resulting in lower capital cost. The use of a steam power generation system allows for efficient utilisation of heat generated in the exothermic partial oxidation and synthesis gas conversion reactions. High temperature heat is retained for steam generation while adiabatic low temperature heat can be used for feedwater preheating.

It will be understood by those skilled in the art that the invention is not restricted to the specific details described above and that numerous modifications and variation can be made without departing from the scope and equivalence of the following claims.

What we claim is:

1. In a process for the utilization of a hydrocarbon feedstock by partially oxidizing the feedstock with oxygen to form a synthesis gas comprising carbon monoxide and hydrogen and subjecting the synthesis gas to a conversion process comprising an exothermic reaction, said oxygen being provided by air separation in which the feed air is at least partially compressed by work generated by expansion of a working fluid vaporized by indirect heat exchange with at least one of the synthesis gas and the exothermic reaction, the improvement consisting in that the working fluid is preheated by indirect heat exchange with adiabatically compressed feed air.

2. The process according to claim 1 wherein said air separation is cryogenic air separation.

3. The process according to claim 2 wherein said natural gas is in a remote location.

4. The process according to claim 1 wherein said feedstock is natural gas.

5. The process according to claim 1 wherein the exothermic reaction is a catalytic hydrogenation.

6. The process according to claim 5 wherein said catalytic hydrogenation is a Fischer-Tropsch synthesis producing paraffinic hydrocarbons.

7. The process according to claim 5 wherein said catalytic hydrogenation produces methanol.

8. The process according to claim 5 wherein said catalytic hydrogenation produces dimethylether.

9. The process according to claim 1 wherein the carbon monoxide:hydrogen mole ratio of the synthesis gas is from about 1:1.6 to about 1:2.5.

10. The process according to claim 1 wherein the working fluid is water.

11. The process according to claim 1 wherein the working fluid is vaporized by indirect heat exchange with the synthesis gas.

12. The process according to claim 1 wherein the working fluid is vaporized by indirect heat exchange with the exothermic reaction.

13. The process according to claim 1 wherein a first vaporized working fluid stream at a first pressure is provided by indirect heat exchange with the exothermic reaction and a second vaporized working fluid stream at a higher pressure is provided by indirect heat exchange with the synthesis gas and both vaporized working fluid streams are expanded to contribute to air compression requirement work.

14. The process according to claim 13 wherein the exothermic reaction heat exchange is supplied with liquid working fluid at least partially preheated by indirect heat exchange with the adiabatically compressed air.

15. The process according to claim 13 wherein the synthesis gas heat exchange is supplied with liquid working fluid at least partially preheated by indirect heat exchange with the adiabatically compressed air.

16. In a process for the utilization of natural gas by partially oxidizing the natural gas with oxygen to form a synthesis gas comprising carbon monoxide and hydrogen and subjecting the synthesis gas to an exothermic catalytic hydrogenation reaction, said oxygen being provided by cryogenic separation of air in which the feed air is at least partially adiabatically compressed by work generated by expansion of steam vaporization by indirect heat exchange with at least one of the synthesis gas and the exothermic reaction, the improvement consisting in that feedwater for said steam vaporization is preheated by heat exchange with the adiabatically compressed feed air.

17. In a process for producing paraffinic hydrocarbons from natural gas by partially oxidizing the natural gas with oxygen to form a synthesis gas comprising carbon monoxide and hydrogen and subjecting the synthesis gas to a Fisher-Tropsch reaction, said oxygen being provided by cryogenic separation of air in which the feed air is at least partially adiabatically compressed by work generated by expansion of steam vaporization by indirect heat exchange with at least one of the synthesis gas and the Fischer-Tropsch reaction, the improvement consisting in that feedwater for said steam vaporization is preheated by heat exchange with the adiabatically compressed feed air.

18. In a process for producing methanol from natural gas by partially oxidizing the natural gas with oxygen to form a synthesis gas comprising carbon monoxide and hydrogen and subjecting the synthesis gas to a catalytic hydrogenation reaction producing methanol, said oxygen being provided by cryogenic separation of air in which the feed air is at least partially adiabatically compressed by work generated by expansion of steam vaporization by indirect heat exchange with at least one of the synthesis gas and the hydrogenation reaction, the improvement consisting in that feedwater for said steam vaporization is preheated by heat exchange with the adiabatically compressed feed air.

19. In a process for producing dimethylether from natural gas by partially oxidizing the natural gas with oxygen to form a synthesis gas comprising carbon monoxide and hydrogen and subjecting the synthesis gas to a catalytic hydrogenation reaction producing dimethylether, said oxygen being provided by cryogenic separation of air in which the feed air is at least partially adiabatically compressed by work generated by expansion of steam vaporization by indirect heat exchange with at least one of the synthesis gas and the hydrogenation reaction, the improvement consisting in that feedwater for said steam vaporization is preheated by heat exchange with the adiabatically compressed feed air.

20. In an apparatus for the utilization of a hydrocarbon feedstock comprising a feedstock reactor for partially oxidizing the feedstock with oxygen to form a synthesis gas comprising carbon monoxide and hydrogen; a synthesis gas conversion reactor for subjecting the synthesis gas to a conversion process comprising an exothermic reaction; an air separation unit for separation of air to supply oxygen to the feedstock reactor and including a feed air compressor; a working fluid circuit including vaporization means for vaporizing the working fluid by indirect heat exchange with at least one of the synthesis gas and the exothermic reaction and an expander for producing work by expansion of the vaporized working fluid; and means coupling said expander to the feed air compressor whereby the feed air is at least partially adiabatically compressed by work generated by the expander, the improvement consisting in that the feed air compressor is an adiabatic compressor providing heated air for preheating the working fluid and the working fluid circuit includes a heat exchanger for indirect heat exchange between the adiabatically compressed feed air and the working fluid to preheat the working fluid and conduit means for conveying said preheated working fluid to said vaporization means.

21. In an apparatus for the utilization of natural gas comprising a feedstock reactor for partially oxidizing the natural gas with oxygen to form a synthesis gas comprising carbon monoxide and hydrogen; a synthesis gas conversion reactor for subjecting the synthesis gas to an exothermic catalytic hydrogenation reaction; an air separation unit for separation of air to supply oxygen to the feedstock reactor and including a feed air compressor; a working fluid circuit including vaporization means producing steam by indirect heat exchange with at least one of the synthesis gas and the exothermic reaction and an expander for producing work by expansion of the steam; and means coupling said expander to the feed air compressor whereby the feed air is at least partially adiabatically compressed by work generated by the expander, the improvement consisting in that the feed air compressor is an adiabatic compressor providing heated air for preheating feedwater to said vaporization means and the working fluid circuit includes a heat exchanger for indirect heat exchange between the adiabatically compressed feed air and feedwater to preheat feedwater and conduit means for conveying said preheated feedwater to said vaporization means.

22. In an apparatus for producing paraffinic hydrocarbons from natural gas comprising a feedstock reactor for partially oxidizing the natural gas with oxygen to form a synthesis gas comprising carbon monoxide and hydrogen; a Fischer-Tropsch reactor for converting the synthesis gas to paraffinic hydrocarbons; an air separation unit for separation of air to supply oxygen to the feedstock reactor and including a feed air compressor; a working fluid circuit including vaporization means producing steam by indirect heat exchange with at least one of the synthesis gas and Fischer-Tropsch reaction and an expander for producing work by expansion of the steam; and means coupling said expander to the feed air compressor whereby the feed air is at least partially adiabatically compressed by work generated by the expander, the improvement consisting in that the feed air compressor is an adiabatic compressor providing heated air for preheating feedwater to said vaporization means and the working fluid circuit includes a heat exchanger for indirect heat exchange between the adiabatically compressed feed air and feedwater to preheat feedwater and conduit means for conveying said preheated feedwater to said vaporization means.

23. In an apparatus for producing methanol from natural gas comprising a feedstock reactor for partially oxidizing the natural gas with oxygen to form a synthesis gas comprising carbon monoxide and hydrogen; a catalytic hydrogenation reactor for converting the synthesis gas to methanol; an air separation unit for separation of air to supply oxygen to the feedstock reactor and including a feed air compressor; a working fluid circuit including vaporization means producing steam by indirect heat exchange with at least one of the synthesis gas and the hydrogenation reaction and an expander for producing work by expansion of the steam; and means coupling said expander to the feed air compressor whereby the feed air is at least partially adiabatically compressed by work generated by the expander, the improvement consisting in that the feed air compressor is an adiabatic compressor providing heated air for preheating feedwater to said vaporization means and the working fluid circuit includes a heat exchanger for indirect heat exchange between the adiabatically compressed feed air and feedwater to preheat feedwater and conduit means for conveying said preheated feedwater to said vaporization means.

\* \* \* \* \*